United States Patent [19]
Alkan et al.

[11] Patent Number: 5,158,804
[45] Date of Patent: * Oct. 27, 1992

[54] PARTICLE COATING APPARATUS FOR SMALL-SCALE PROCESSING

[75] Inventors: M. Hayat Alkan, Chicago; Michael J. Groves, Lincolnshire, both of Ill.

[73] Assignee: Board of Trustees of the University of Illinois

[*] Notice: The portion of the term of this patent subsequent to Apr. 24, 2007 has been disclaimed.

[21] Appl. No.: 511,565

[22] Filed: Apr. 20, 1990

Related U.S. Application Data

[63] Continuation-in-part of Ser. No. 109,229, Oct. 16, 1987, Pat. No. 4,919,973.

[51] Int. Cl.$^5$ .............................................. B05D 7/00
[52] U.S. Cl. ................................... 427/213; 118/303; 118/DIG. 5; 427/3; 427/600
[58] Field of Search ................. 427/185, 213, 57, 212, 427/3; 118/DIG. 5, 303

[56] References Cited

U.S. PATENT DOCUMENTS

| | | |
|---|---|---|
| 2,667,806 | 2/1954 | Morse et al. |
| 4,644,665 | 2/1987 | Naunapper et al. ............ 427/213 X |
| 4,656,056 | 4/1987 | Leuenberger . |
| 4,685,419 | 8/1987 | Nakajima ...................... 118/DIG. 5 |
| 4,919,973 | 4/1990 | Alkan et al. .......................... 427/213 |

FOREIGN PATENT DOCUMENTS 45-37123  11/1970  Japan .

OTHER PUBLICATIONS

Seitz, J. A., et al.,: Ch. 12: Tablet Coating in *The Theory and Practice of Industrial Pharmacy*, 3rd Ed., Edited by L. Lachman, et al., Lea and Febiger, Philadelphia, pp. 346–373 (1986).

*Primary Examiner*—Shrive Beck
*Assistant Examiner*—Terry J. Owens
*Attorney, Agent, or Firm*—Marshall, O'Toole, Gerstein, Murray & Bicknell

[57] ABSTRACT

Apparatus and methods are provided for coating relatively small quantities of particles including tablets, pellets, or granules. The device effectively fluidizes the particles to be coated by controlled vibration of a perforated platform through which drying air is passed during intermittent spraying of the particles with a solution of organic or aqueous-based coating material. The method coats individual tablets having as low a mass as 50 mg and coats quantities ranging from less than about 50 mg to 10 g of tablets, pellets, or granules.

21 Claims, 5 Drawing Sheets

PARTICLE COATING APPARATUS FOR SMALL-SCALE PROCESSING

CROSS-REFERENCE TO RELATED APPLICATIONS

The present invention is a continuation-in-part of co-pending U.S. Pat. application Ser. No. 07/109,229, filed Oct. 16, 1987, now U.S. Pat. No. 4,919,973.

BACKGROUND OF THE INVENTION

The present invention relates generally to systems for coating relatively small quantities of variously shaped materials and more particularly to systems for preparing coated tablets, pellets, or granules in quantities of from less than about 50 mg to 10 g. In a preferred embodiment, the present invention provides devices which effectively fluidize particulate materials, to be spray coated, by controlled vibration of a perforated bed through which drying air is passed. The methods and apparatus provided by the present invention allow for small-scale production of coated tablets, pellets or granules and are especially useful in dealing with small quantities of scarce or expensive materials, e.g., drugs during the initial stages of formulation and development.

The preparation of coated tablets, pellets, and granules is a common pharmaceutical process used to mask the taste of a drug, to improve drug appearance and stability, and/or to control drug release. See, e.g., Seitz, J.A., et al.,: Ch. 12: Tablet Coating in *The Theory and Practice of Industrial Pharmacy*, 3rd Ed. Edited by L. Lachman, et al., Lea and Febiger, Philadelphia, 1986. The coatings are commonly applied by spraying solutions of coating material into rotating drums containing the solid dosage form of the drug or by spraying coating solutions into fluidized or spouting beds, such as Wurster columns. Fluidization of the materials to be coated is ordinarily achieved in a columnar chamber by the upward flow of drying air. While these methods are generally effective for large-scale production, they are not readily applied in small scale contexts where the drug to be coated is either not readily available in large quantities and/or is relatively expensive. The smallest rotating drum method currently available is believed to require use of at least 10–100 g of material to be coated and the smallest fluid bed devices currently available are believed to require a minimum of about 0.5 kg of material.

In sum, no prior devices or methods have been totally responsive to the need in the art for devices and methods allowing for the coating of small particles in quantities of ten grams or less.

BRIEF SUMMARY OF THE INVENTION

The present invention provides an improved apparatus and methods for the uniform application of one or more layers of coating materials to variously shaped particles, which apparatus and methods are quite advantageously applied to small (50 mg to 10 g) quantities of particles. According to these improved apparatus and methods, particles to be coated are fluidized by application of vibratory energy of selected amplitude and frequency in the course of spray coating and drying.

Apparatus of the present invention is seen to generally comprise a container, for the particle(s) to be coated, having a particle support means at its base and further having a means for providing vibratory energy to the support. The support has an upper and a lower side and supports the particle(s) to be coated on the upper side. The apparatus also includes means for applying fluid coating materials to the particles (preferably in the form of an airbrush sprayer) as well as means for supplying gas flow to the particles (preferably air and optionally intermittent). In operation, particles are disposed on the support and caused to vibrate and to become fluidized during application of the coating material and during application of a drying gas flow to the particles. Intermittent application of coating materials during essentially continuous application of vibratory energy and/or gas flow results in development of uniform multilamellar coating of particles.

As conventionally used, the term "fluidization" includes processes where solid particles are throughly agitated and the entirety of the mass takes on the appearance of a boiling liquid, sometimes referred to as a "pseudo liquid". Fluidization is generally used to promote an interfacial chemical reaction between a solid phase and a gas phase. Through fluidization, an entire powder system is able to flow like a liquid such that individual particles in the system are individually surrounded by gas and the normal mechanical constraints on the movement of individual particles in the system are removed. The degree of particle separation required in a process for effectively contacting particles with reactant gas is not as great as the amount of separation required in a process for the effective coating of particles.

As used herein, the term "fluidization" is meant to encompass that process which requires a greater separation of the individual particles to afford complete and uniform coating of each individual particle. The separation of particles required for coating is greater than that required for allowing particles to come in contact with a gas. The fluidized thin layer generated by the relative dimensions of the apparatus and the amount of particulate to be coated cannot effectively be fluidized by air flow because the velocity of air flow required to achieve fluidization would cause the contents of a down-scaled apparatus to spout beyond the confines of the apparatus. The apparatus of the invention has the capacity to accommodate a thin layer of particulate which is then effectively fluidized by vibration.

In preferred configurations, the support provided at the base of the container has upper and lower sides (the particles being supported on the upper side) and is perforated. Gas flow for drying of the particles is supplied to the lower side of the support and flows upwardly through the perforations. In an alternative conformation, gas flow may be provided by providing a decreased pressure beneath the perforated support, drawing, e.g., air, downwardly through the perforations.

The fluidizing vibratory energy can be supplied by a transducer for the conversion of electrical energy to mechanical energy, e.g., by a loudspeaker. Amplitude can be controlled by an amplifier and frequency can be controlled with a wave generator, e.g., a sine wave/-square wave generator. The shape of the wave generated can be adjusted to achieve more uniform coatings. Generally, square wave generation "bounces" the objects being coated higher off the support than sine wave generation and results in improved, more uniform, coatings.

The coating material(s) can be applied continuously or intermittently during the supply of vibratory energy and the supply of drying gas flow. The supply of vibratory energy may also be continuous or intermittent, as may the supply of drying gas flow. The coatings may be applied to the upper side of the vibrating bed by means of e.g., an airbrush.

The overall scale of the apparatus is such as to allow for batch coating of from about 0.050 g to about 10 g of particles. The dimensions and functioning of the apparatus are such that thin layers of particulate material, at opposed to tall columns of material, can be effectively coated. The particles may be variously shaped and may have an individual mass of less than 100 mg.

The invention also provides for a novel method for coating a thin layer of variously shaped particles comprising the steps of: fluidizing the particles by applying vibratory energy of an effective amplitude and frequency (such that the fluidizing does not employ gas flow for fluidization), spraying coating materials onto the particles, and sujecting particles to a gas flow to dry the coated particles. The vibratory energy can comprise electrical energy transduced to mechanical energy, for example by using a loudspeaker. Also, the vibratory energy can comprise using a wave generator such as a sine wave/square wave generator and can be amplified using an amplifier.

The coating process is rapid, quantitative, and economical and may be used with aqueous or organic solvent based systems. Further, the invention advantageously allows for gravimetric measurement of the amount of coating applied. The method of small-scale coating is especially useful when dealing with small quantities of expensive drugs at the initial stages of formulation and development.

Granules coated according to the invention with aqueous or organic solutions of acrylic resins, such as Eudragits TM RL100, L100-55, and L30D, are attractive in appearance and the coating load achieved proportionally affects the delay in the release of an incorporated drug, such as quinacrine dihydrochloride.

Other aspects and advantages of systems of the present invention will be apparent upon consideration of the following detailed description thereof which includes numerous illustrative examples of the practice of the invention, reference being made to the drawing wherein.

DETAILED DESCRIPTION

The following examples illustrate practice of the invention by which the small-scale coating of particles, including tablets, pellets, or granules, in quantities of from less than about 50 mg to 10 g, is achieved. More specifically, Example 1 illustrates the assembly of the coating apparatus; Example 2 illustrates the preparation of model compound granules to be coated; Example 3 relates to exemplary coating procedures employing the apparatus of Example 1; and, Example 4 describes the dissolution testing of products.

The examples which follow are for illustrative purposes are not intended in any way to limit the scope of the invention.

EXAMPLE 1

Figure 1:
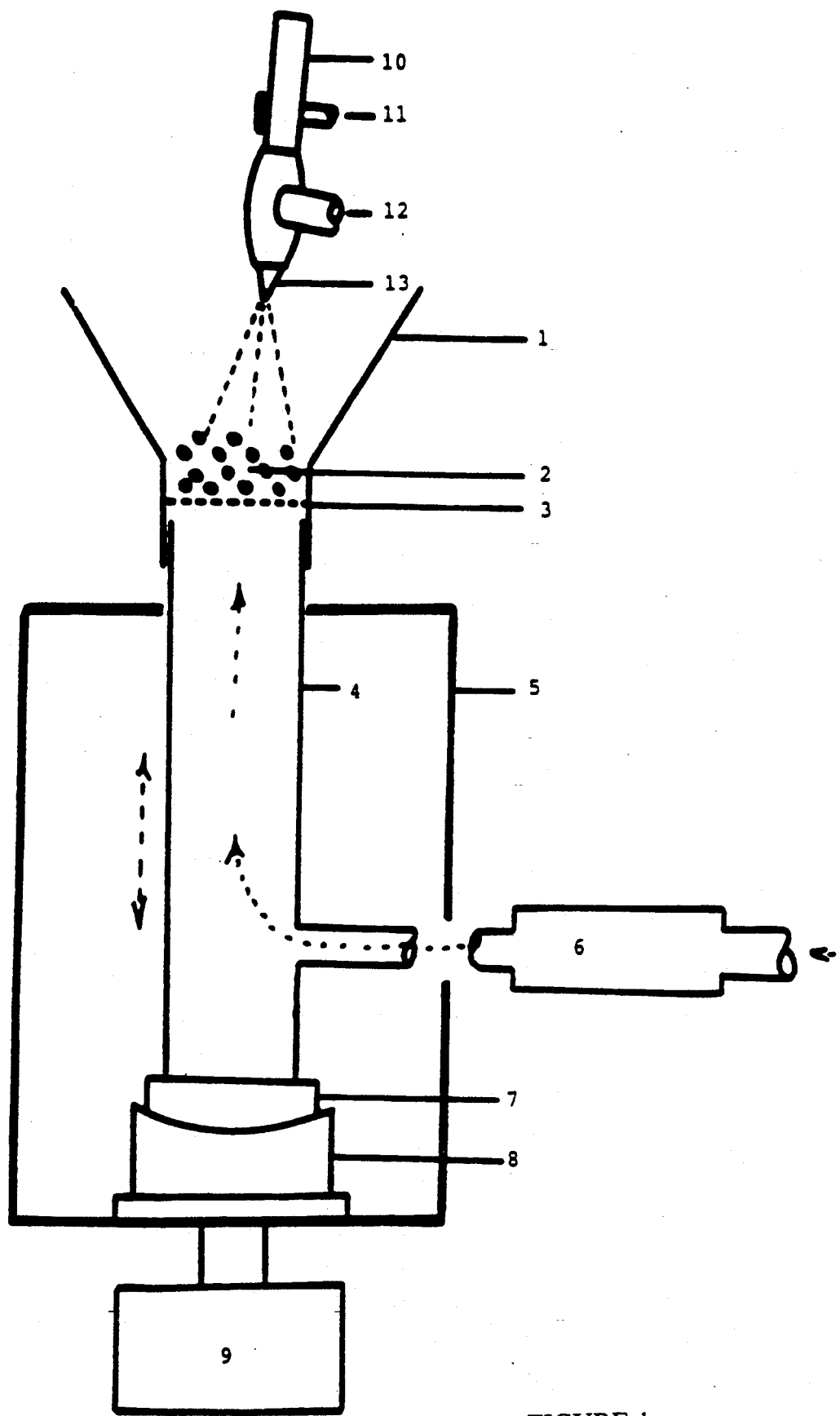
FIG. 1 is a sectional view of the apparatus of the invention.

FIG. 1 depicts a schematic diagram of a small-scale coating device (1) polyethylene funnel; (2) fluidized particulate; (3) 35 mesh sieve to support particulate; (4) supporting tube; (5) supporting framework; (6) drying air inlet and Drierite TM tube; (7) metal lid glued onto amplifier loudspeaker diaphragm; (8) amplifier having a loudspeaker output; (9) driver amplifier; (10) airbrush; (11) air inlet; (12) coating solution; (13) binary nozzle.

In a preferred embodiment, the conical funnel (1) is made of polyethylene and has an upper internal diameter of 100 mm and a lower internal diameter of 40 mm. The funnel is cut at the apex of the core, and a 35 mesh polyethylene sieve (3) inserted between the upper and lower portions and glued into position (polyisothiocyanate cement, Krazy Glue Inc., Itasca, IL).

The funnel (1) is supported on a parallel sided polyethylene tube (4), 40 mm external diameter to provide a close fit. The tube (4) has a side piece connected, through a silicon rubber tube and a cylinder (6) of indicating Drierite TM silica gel, to a tank of compressed gas (e.g., air). At the lower end, the tube (4) is glued to a metal screw capped lid (7), 70 mm diameter, itself glued to an elastomeric membrane, such as that of a loudspeaker (8). In both cases, the adhesive used is a silicon rubber cement (Dow, Midland, MI).

In this embodiment, the loudspeaker (8) is a 10 cm Realistic (Radio Shack) woofer speaker (model number 40-1022), 5W nominal power over a range of 55-5000 Hz. Amplitude adjustment is achieved with a (9) Realistic TM Model SA-15 Integrated Stereo Amplifier. Frequency is controlled with a Dynascan Corp B and K Precision Solid State Model E-310B sine/square wave generator, forming a part of amplifier (9). The shape of the wave generated influences the vibration generated which in turn influences the uniformity and thickness of the coating achieved. When the amplitude is plotted as a function of time, the resultant curve is either a sinusoidal waive or a square wave. Generally, the square wave curve is more advantageous for making the objects being coated "bounce" higher off the support sieve. Generally, this results in achieving more uniform coatings.

Calibration of both amplitude and frequency is obtained by vertically moving a paper chart at a predetermined speed past a pen attached to the upper part of the funnel (1).

Coating solutions are applied to the upper side of the vibrating support sieve by means of a Paasche TM artists' airbrush (10), using jets as appropriate, and driven by a compressed air tank.

EXAMPLE 2

Granules are prepared from quinacrine dihydrochloride (Aldrich Chemical Co.) and lactose or soy protein (food grade soy protein isolate-ARDEX R TM, Archer, Daniel Midland) by wet granulation using a 60% aqueous sucrose syrup or water, forced through a 3.36 mm stainless steel mesh and dried at 25°±1° C. overnight. Dried granules are separated into fractions using a 3" vibratory sieve shaker (Gilson, Model SS-5) through sieves with apertures varying from 0.075 to 2.83 mm. Granules prepared using PVP (Polyvinyl Pyrrolidone, GAF Corporation) as a binder are too fragile to be vibrated during the coating process. Testing is carried out on two basic granule formulations consisting of either:

|    |                          |        |
|----|--------------------------|--------|
|    | quinacrine dihydrochloride | 19.2 g |
|    | lactose                  | 72.0 g |
|    | sucrose (as syrup) dry weight | 8.9 g |
| or |                          |        |
|    | quinacrine dihydrochloride | 20.0 g |
|    | soy protein              | 80.0 g |
|    | water                    | 9.5 g  |

EXAMPLE 3

Coating solution was manually applied by positioning the nozzle of the airbrush a suitable distance (e.g., 5-7 cm) from the surface of the bed and using short, three to five second bursts at 2 minute intervals to allow each consecutive coat to dry. Exemplary coating solutions used included:

Eudragit TM RL100, 6 to 9% w/v in chloroform;
Eudragit TM L30D in 20% aqueous propylene glycol; and
Eudragit TM L100-55 30% w/v dissolved in aqueous 1N sodium hydroxide.

A thin coating of Eudragit TM RL100 is first applied, before application of the aqueous soluble coatings, to avoid dissolving the water soluble granule constituents, for example lactose. Coating is carried out at ambient room temperature (approximately 25° C.) in a chemical fume hood and is continued until a required mass/unit area of coating has been built up on the granules or until the requisite amount of coating has been applied as determined from the weight increase of the granules.

Depending on the quantity and size of the material to be coated, the amplitude and frequency of the vibration of the sieve support (mesh grid) can be varied widely and is empirically adjusted to obtain uniform coatings while allowing the bed to oscillate without material spilling out and over the sides of the funnel. Thus, the amplitude of the sieve support can range from 0.05 mm to 50 mm and preferably from 0.5 mm to 10 mm; the frequency ranges from 10 to 1000 Hz and preferably from 10 to 100 Hz. In addition, the wave generator can be set to either the "square" or "sine" position. It has been found that when the wave generator is set at the "square" setting that the material to be coated bounces significantly higher off the mesh grid (approximately from 10 to 20 percent higher than that observed at the "sine" setting). It has also been found that improved, more uniform, coatings are obtained at this "square" setting.

The velocity and temperature of the drying air [through (6)] can also be adjusted to accommodate various coating solutions according to the solvent used in the particular coating solution required. Depending on the material to be coated, these parameters can all be varied to obtain products optimally coated.

A typical set of conditions for a 1 g load of lactose granules, mean, diameter 1.85 mm, sprayed with a solution of Eudragit TM RL100 6% in chloroform is as follows:

| amplitude | 3.25 mm |
|-----------|---------|
| frequency | 23 Hz |
| drying air pressure | 12 psig |
| spray air pressure | 5 psig |

-continued

| spray nozzle closure setting | 1.5 turns |
|---|---|

EXAMPLE 4

Dissolution testing was carried out according to the USP XXI, Apparatus 2, method with the paddles rotating at 50 rpm in 1 L distilled water or phosphate buffer at 37° C. as the dissolution medium. The apparatus is a six station Vanderkamp ® model 600 USP dissolution tester with a VanKel Model 2500 external circulator and an auto sampling peristaltic driving pump, all by VanKel Industries Inc. Absorbance at 425 nm is continuously determined throughout the dissolution run by means of a Perkin-Elmer Lambda TM 3B uv/vis spectrophotometer fitted with a Model 3600 data station and Model 660 printer. Dissolution rates for comparative studies are estimated and are defined as the time required for 50% or 15% ($t_{50}$, $t_{15}$) of the drug to be released.

Initial experiments using beeswax containing methylene blue as a coating indicated that this type of coat was less even and regular than desired. Examination under a low power microscope revealed some folds, cracks, and cavities in the coatings. However, coatings with the Eudragit TM resins are visually glossy and uniform in appearance under the microscope. Generally, batches of particles weighing from approximately 0.1 g to 10 g can be successfully coated according to the device and method of the invention. Individual particles ranging in size from approximately 100 microns to approximately several mm in length have been successfully coated; in addition individual tablets weighing as little as 100 mg may also successfully be coated, as may small, 50 mg, compacted pellets.

Figure 2:
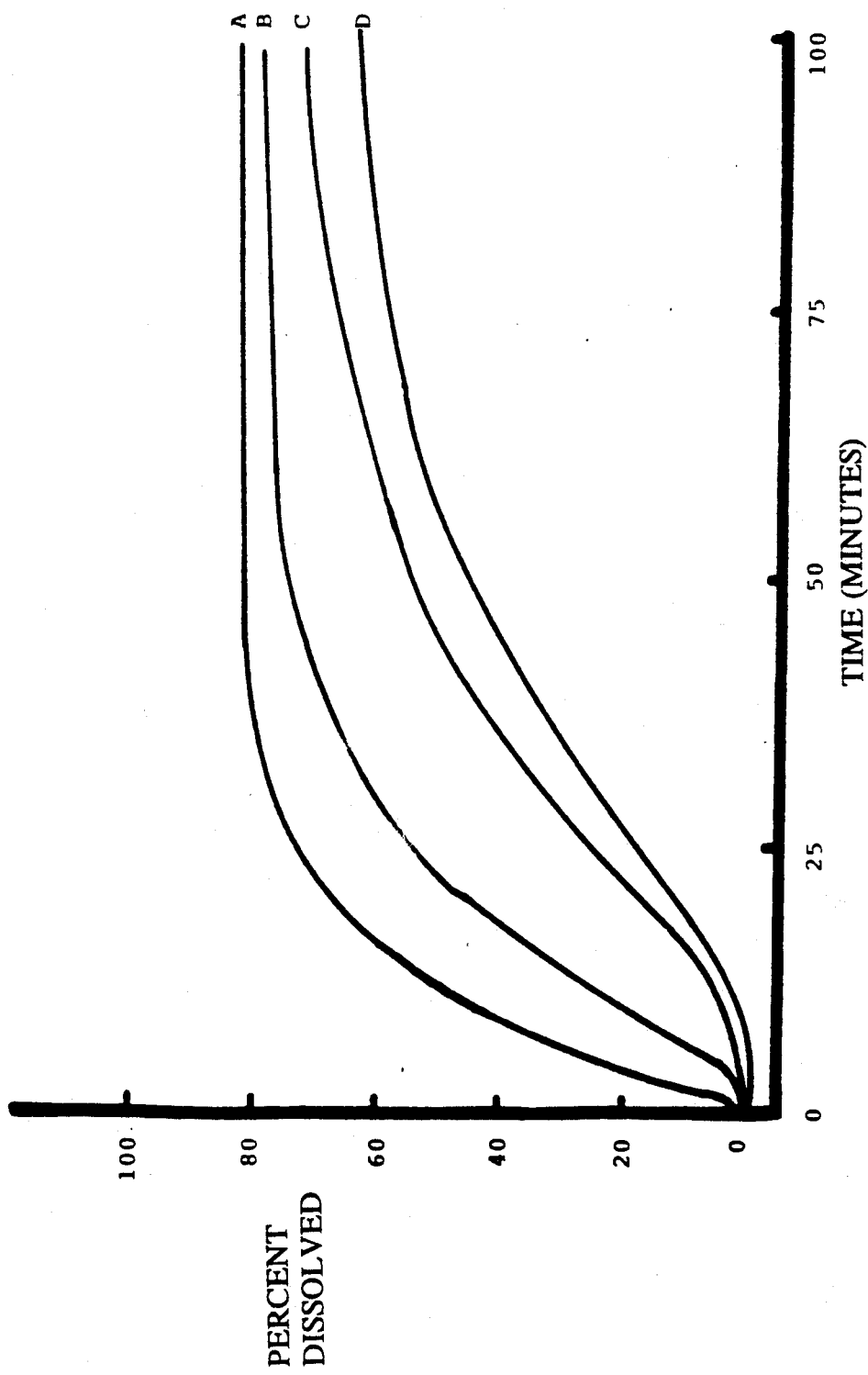
FIGS. 2 and 3 are graphic representations of dissolution profiles of granules coated according to the invention.
Figure 3:
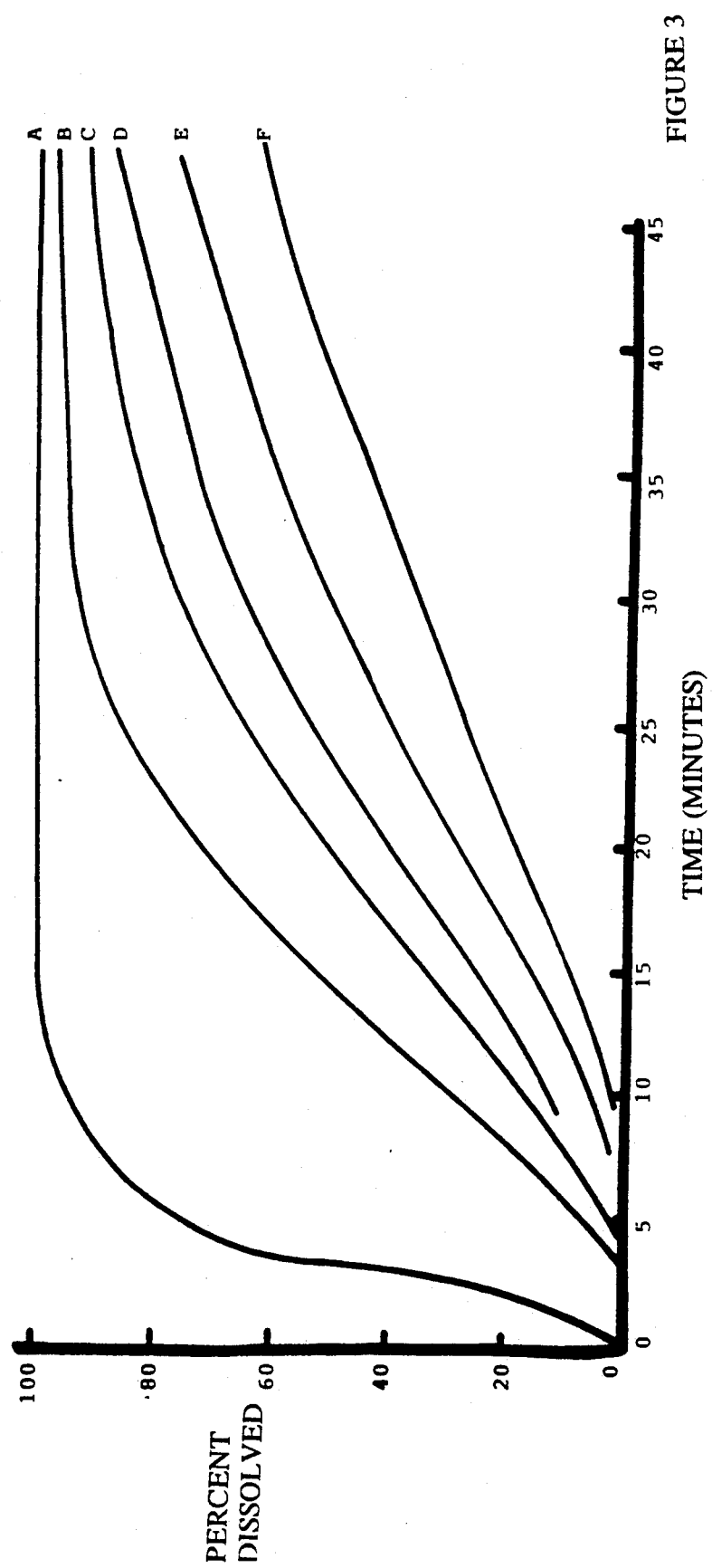

FIG. 2 depicts the dissolution profiles obtained for granules containing quinacrine dihydrochloride coated with different loading of Eudragit TM RL. The granules made from lactose and sucrose were coated as follows: A. uncoated; B. 3 mg/cm$^2$; C. 6 mg/cm$^2$; and D. 7 mg/cm$^2$. FIG. 3 also depicts dissolution profiles obtained for granules containing quinacrine dihydrochloride coated with different loading of Eudragit TM RL, however, these granules were made from soy protein and were coated as follows: A. uncoated; B. 1.3 mg/cm$^2$; C. 2.3 mg/cm$^2$; D. 3.3 mg/cm$^2$; E. 4.4 mg/cm$^2$; and F. 6.2 mg/cm$^2$.

Figure 4:
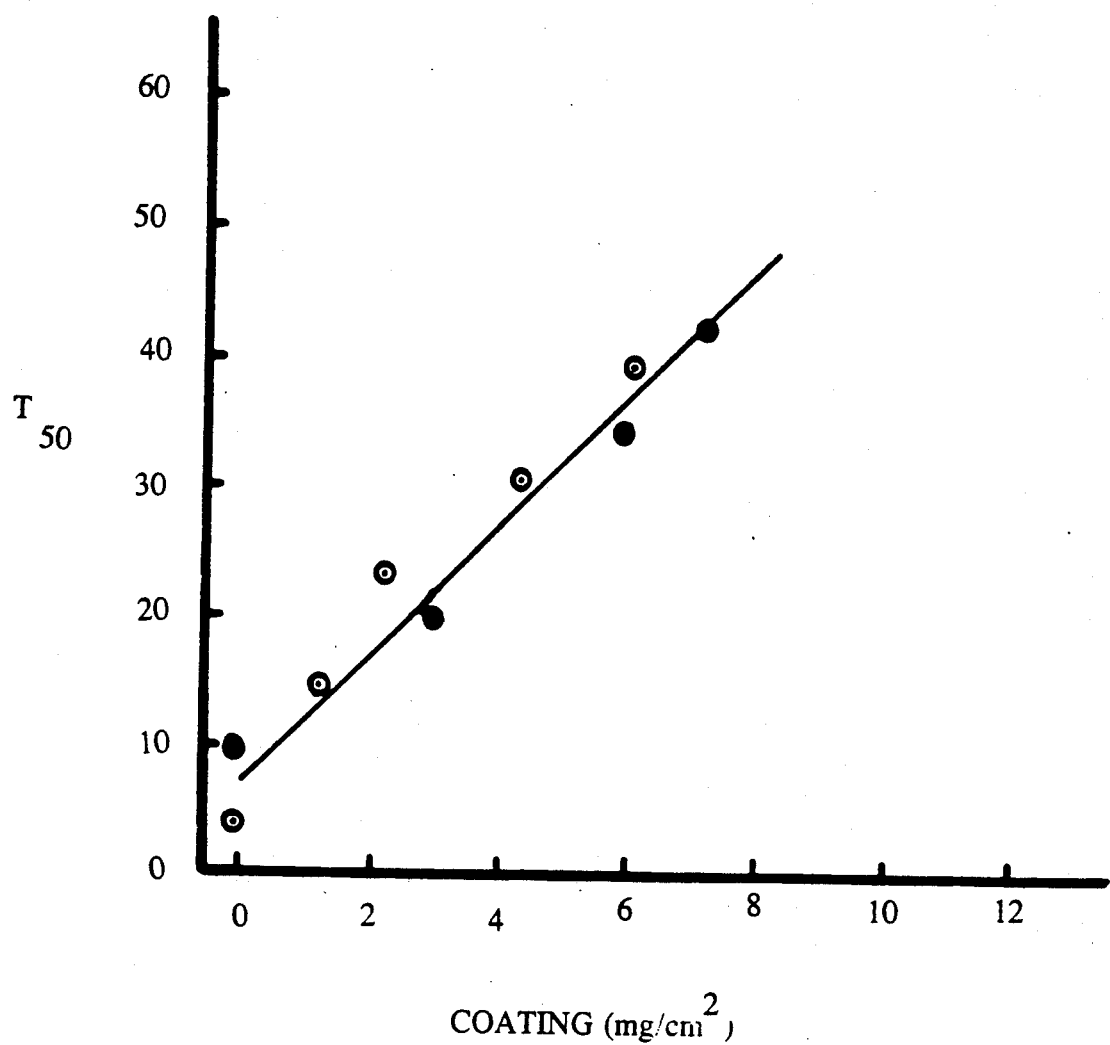
FIG. 4 is a graphic comparison of release rates from different formulations of granules coated with differing thicknesses of coating according to the invention.
Figure 5:
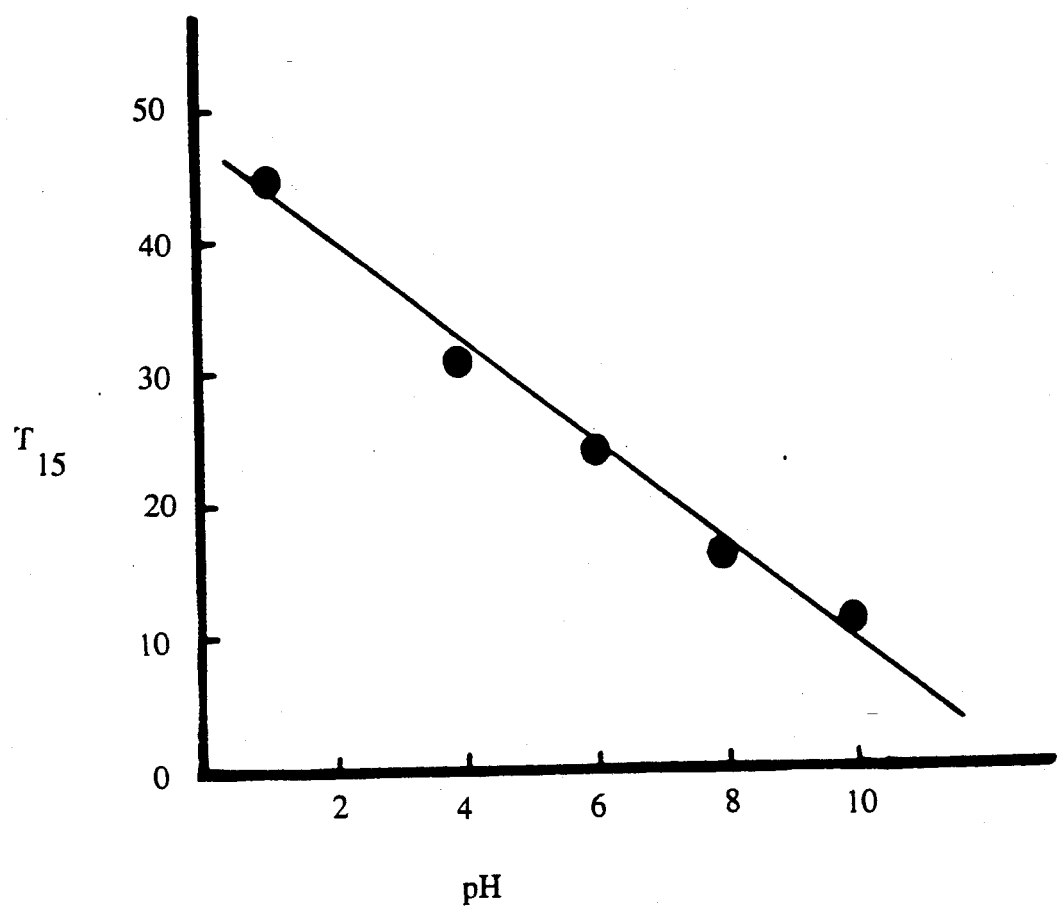
FIG. 5 is a graphic representation of the effect of pH on granules coated with an enteric coating according to the invention.

FIG. 4 shows a comparison of the release rates from different formulations of granules containing quinacrine dihydrochloride as a function of Eudragit TM RL coating and incorporates data from FIGS. 2 and 3: open-circles: lactose/sucrose ($r^2=0.992$); and closed-circles: soy protein ($r^2=0.992$). FIG. 5 shows the effect of pH on the initial ($t_{15}$) release of quinacrine dihydrochloride from lactose/sucrose granules coated with 7.9 mg/cm$^2$ Eudragit TM L30D (mean of duplicate tests) ($r^2=-0.995$).

By increasing the coating load, the dissolution rate of the coated materials is slowed appreciably and predictably as illustrated in FIGS. 2-4. In addition, FIG. 5 illustrates the dissolution rate of granules coated with a pH sensitive material. The release rate of the drug from soluble or insoluble granules coated with a permeable but insoluble film (Eudragit TM RL) decreases directly with an increase in the amount of coating applied and the release process is unaffected by the granule formulation (FIG. 4). The dissolution experiments for enteric coated granules clearly indicate that the rate of release of the drug is a function of the solubility of the coating material (FIG. 5). The dissolution rate as a function of pH is measured only at the initial stages of dissolution, i.e., at 15 minutes, because at later stages, the dissolution process is additionally affected by the decrease in solubility of the drug itself. The drug used in this study is a base and its solubility should be lower at higher pH. However, for the initial stages of dissolution the variable solubility of the drug as a function of pH should not affect the rate of dissolution as long as sink conditions persist. All of these results indicate that an even coat of constant thickness was achieved using the device and method of the invention.

It is noteworthy that if sufficient coats of Eudragit TM are applied to a water soluble particulate material, upon exposure to aqueous conditions the core material dissolves and permeates through the insoluble but permeable coat. Thin hollow shells of the coating are left having the shape of the soluble granule or pellet originally forming the matrix. These shells are completely formed and have no gaps, demonstrating the uniformity with which the coating is applied using the systems of the invention.

As is also true for other fluidization processes, the physical formulation of the particles or granules is quite significant since they must be hard enough to resist abrasion during the tumbling and collisions involved during the vibration phase of the method.

The foregoing illustrative examples relate to a small-scale coating apparatus for coating small amounts of variously shaped particles. While the present invention has been described in terms of a specific device and method, it is understood that variations and modifications will occur to those skilled in the art upon consideration of the present invention.

For example, it is envisioned that methods other than use of a loudspeaker membrane could be used to generate vibratory energy to fluidize the particles to be coated; for example a mechanical oscillatory cam device and a piezo electric device may be equally effective. Also, while the application of a specific film coating has been described, it will be apparent that other coatings such as sugar coatings, syrup coatings, wax coatings, seal coatings, cellulosic and other polymeric coatings may be employed in practice of the invention. Moreover, plasticizers, colorants, and similar additives may readily be incorporated in the coating material. Further, while the coating of drugs has been described, the coating of other small particles, such as precious jewels, pearls, diamonds, electronic components, and small mechanical components, such as ball-bearings and the like, with metal coatings, lubricants, anti-oxidants, gelatins, protective coatings, and the like may readily be accomplished according to the device and method of the invention.

Numerous modifications and variations in the invention as described in the above illustrative examples are expected to occur to those skilled in the art and consequently only such limitations as appear in the appended claim should be placed thereon.

Accordingly, it is intended in the appended claims to cover all such equivalent variations which come within the scope of the invention as claimed.

What is claimed is:

1. An apparatus capable of uniformly coating a thin layer of particles with coating materials, said apparatus comprising:

container means for said particles, said container means having a base;

support means at said container base, having upper and lower sides and capable of supporting a thin layer of said particles on said upper side;

fluidizing means, for fluidizing said particles supported on said upper side, without eh use of gas fluidization, said fluidizing means comprising means for supplying to said support means, vibratory energy of an effective amplitude and frequency sufficient to impart fluidization to said particles;

means for supplying coating material to uniformly coat said fluidized particles; and means for supplying a flow of drying gas to dry said coated particles fluidized by said vibratory energy;

said means for supplying vibratory energy, said means for supplying coating material, and said means for supplying drying gas, comprising means cooperating to uniformly coat said particles with coating material.

2. The apparatus according to claim 1, wherein said support means is perforated and said means for supplying drying gas comprises means for supplying gas flow to the lower side of said perforated support means and upwardly through the perforations therein.

3. The apparatus according to claim 1, wherein said means for supplying vibratory energy comprises a transducer for conversion of electrical energy to mechanical energy.

4. The apparatus according to claim 3, wherein said transducer comprises a loudspeaker.

5. The apparatus according to claim 3, wherein said means for supplying vibratory energy further comprises a wave generator.

6. The apparatus according to claim 5, wherein said wave generator comprises a square wave generator.

7. The apparatus according to claim 5, wherein said wave generator comprises a sine wave generator.

8. The apparatus according to claim 3, wherein said means for supplying vibratory energy further comprises an amplifier.

9. The apparatus according to claim 1, wherein said means for supplying coating materials is susceptible to intermittant operation during supply of vibratory energy and gas flow.

10. The apparatus according to claim 9, wherein said means for supplying coating materials comprises an airbrush.

11. The apparatus according to claim 1, wherein said means for supplying drying gas comprises means susceptible to intermittant operation during the supply of vibratory energy and coating material.

12. The apparatus according to claim 1 wherein said apparatus is capable of batch coating from about 0.050 g to about 10 g of particles.

13. The apparatus according to claim wherein said apparatus is capable of batch coating said particles having an individual mass of less than 100 mg.

14. In a method for coating particles, said method including the steps of:

fluidizing said particles, spraying coating material onto said particles to form coated particles, and subjecting said coated particles to a gas flow to dry said coated particles, the improvement comprising fluidizing said particles, without the use of gas fludization, by applying vibratory energy of an effective amplitude and frequency sufficient to impart fluidization to said particles.

15. The method according to claim 14, wherein said step of applying vibratory energy comprises the step of transducing electrical energy to mechanical energy.

16. The method according to claim 15, wherein said transducing step comprises using a loudspeaker.

17. The method according to claim 14, wherein said step of applying vibratory energy comprises the step of using a wave generator.

18. The method according to claim 17, wherein said step of using a wave generator comprises generating a square wave.

19. The method according to claim 17, wherein said step of using a wave generator comprises generating a sine wave.

20. The method according to claim 14, wherein said step of applying vibratory energy comprises using an amplifier.

21. The method according to claim 14, wherein said improvement further comprises:
supporting said particles in a thin layer.

* * * * *